(12) United States Patent
Gomez, Jr. et al.

(10) Patent No.: US 11,013,632 B1
(45) Date of Patent: May 25, 2021

(54) BACK AND NECK CUSHION THERAPY DEVICE

(71) Applicants: Jose Gomez, Jr., Humble, TX (US); Victor B. Ramos, Houston, TX (US)

(72) Inventors: Jose Gomez, Jr., Humble, TX (US); Victor B. Ramos, Houston, TX (US)

(*) Notice: Subject to any disclaimer, the term of this patent is extended or adjusted under 35 U.S.C. 154(b) by 578 days.

(21) Appl. No.: 15/590,281

(22) Filed: May 9, 2017

Related U.S. Application Data

(63) Continuation-in-part of application No. 13/789,485, filed on Mar. 7, 2013, now abandoned, which is a continuation-in-part of application No. 12/839,293, filed on Jul. 19, 2010, now Pat. No. 8,449,486, and a continuation-in-part of application No. 12/619,230, filed on Nov. 16, 2009, now Pat. No. 8,414,514, and a continuation-in-part of application No. 12/619,279, filed on Nov. 16, 2009, now Pat. No. 8,435,201.

(51) Int. Cl.
| | |
|---|---|
| *A61F 5/048* | (2006.01) |
| *A61F 5/058* | (2006.01) |
| *A61F 5/01* | (2006.01) |
| *A61F 5/04* | (2006.01) |
| *A47C 7/42* | (2006.01) |
| *A45F 3/12* | (2006.01) |

(52) U.S. Cl.
CPC .......... *A61F 5/048* (2013.01); *A61F 5/05816* (2013.01); *A45F 2003/122* (2013.01); *A47C 7/42* (2013.01); *A61F 5/01* (2013.01); *A61F 5/012* (2013.01); *A61F 5/04* (2013.01)

(58) Field of Classification Search
CPC ...... A61F 5/042; A61F 5/048; A61F 5/05816; A61F 5/04; A61F 5/01; A61F 5/012; A61F 5/026; A61F 5/028; A47C 7/42; A45F 2003/122

USPC ....... 602/32, 36, 37; 601/134–138, 143–147, 601/124, 128, 131–32, 56; 5/632–633, 5/640, 657; 482/91; 297/284.1–284.11, 297/219.12, 397; 2/463–464, 467
See application file for complete search history.

(56) References Cited

U.S. PATENT DOCUMENTS

| | | | |
|---|---|---|---|
| 395,043 A | 12/1888 | Doremus | |
| 1,549,601 A * | 8/1925 | Mulgrew | A47C 7/40 5/632 |
| 2,765,480 A | 10/1956 | Mueller | |
| 2,973,030 A * | 2/1961 | Matthewson | B60N 2/7005 297/393 |
| 3,348,880 A * | 10/1967 | Swann | B60N 2/914 297/228.13 |
| 3,611,444 A | 10/1971 | Rector | |

(Continued)

OTHER PUBLICATIONS

Ward, John, Anterior-to-posterior Protective Capabilities of the Spine Buddy Jockey Vest Support Pad, Topics in Integrative Health Care [Issn 2158-4222]—vol. 5(4), Dec. 31, 2014.

(Continued)

*Primary Examiner* — Tarla R Patel
(74) *Attorney, Agent, or Firm* — Rao DeBoer Osterrieder, PLLC; Dileep P. Rao

(57) ABSTRACT

A cushion therapy device including a body, wherein the body has a channel formed therein. The cushion therapy device has a lower member and an upper member, each connected with the body. The cushion therapy device can have additional attachments and sensors for therapeutic relief.

8 Claims, 3 Drawing Sheets

(56) References Cited

U.S. PATENT DOCUMENTS

| | | | |
|---|---|---|---|
| 4,397,046 A * | 8/1983 | Steiner | A41D 13/018 2/44 |
| 4,876,755 A * | 10/1989 | Parrish | A47C 7/425 297/284.3 |
| 5,007,413 A | 4/1991 | Aalvik Thune | |
| 5,503,456 A | 4/1996 | Rossini | |
| 5,713,841 A * | 2/1998 | Graham | A61H 1/0218 602/32 |
| 6,050,265 A * | 4/2000 | Richardson | A61G 7/065 128/845 |
| 6,182,311 B1 | 2/2001 | Buchanan et al. | |
| 6,258,050 B1 | 7/2001 | Henderson | |
| 6,357,066 B1 * | 3/2002 | Pierce | A61B 6/0442 5/710 |
| 7,048,703 B2 | 5/2006 | Riach | |
| 7,059,678 B1 * | 6/2006 | Taylor | A47C 7/405 297/284.4 |
| 7,137,961 B2 | 11/2006 | Hurd | |
| 7,378,975 B1 * | 5/2008 | Smith | A61B 5/1126 340/573.1 |
| 7,634,829 B1 | 12/2009 | La Bar | |
| 7,703,849 B2 * | 4/2010 | Bilak | A47C 7/462 297/230.13 |
| D639,961 S | 6/2011 | Gomez, Jr. et al. | |
| 8,414,514 B2 | 4/2013 | Gomez, Jr. et al. | |
| 8,435,201 B2 | 5/2013 | Gomez, Jr. et al. | |
| 8,449,486 B2 * | 5/2013 | Gomez, Jr. | A61F 5/048 128/106.1 |
| 2003/0013996 A1 * | 1/2003 | Chen | A61H 23/0263 601/46 |
| 2008/0066233 A1 | 3/2008 | Russell | |
| 2008/0150337 A1 | 6/2008 | Bilak et al. | |
| 2009/0198163 A1 | 8/2009 | Senyei et al. | |

OTHER PUBLICATIONS

Ward, John, and Jesse Coats, Ice Pack-Cooled Ergonomic Chair Support Impact on Spine Pain and Flexion-Relaxation Phenomenon: A Pilot Study, Topics in Integrative Health Care 2016, vol. 7(1), Jun. 24, 2016.

* cited by examiner

BACK AND NECK CUSHION THERAPY DEVICE

CROSS REFERENCE TO RELATED APPLICATIONS

The present application is a Continuation in Part of co-pending U.S. patent application Ser. No. 13/789,485 filed on Mar. 7, 2013, entitled "BACK AND NECK CUSHION THERAPY DEVICE", which is a Continuation in Part of U.S. patent application Ser. No. 12/839,293 filed on Jul. 19, 2010, entitled "BACK AND NECK CUSHION THERAPY DEVICE", issued as U.S. Pat. No. 8,449,486 on May 28, 2013, a Continuation in Part of U.S. patent application Ser. No. 12/619,230 filed on Nov. 16, 2009, entitled "WEARABLE AMBULATORY TRACTION SYSTEM", issued as U.S. Pat. No. 8,414,514 on Apr. 9, 2013, and a Continuation in Part of U.S. patent application Ser. No. 12/619,279 filed on Nov. 16, 2009, entitled "METHOD FOR TREATING A USER'S BACK OR NECK USING A TRACTION SYSTEM", issued as U.S. Pat. No. 8,435,201 on May 7, 2013. These references are incorporated herein in their entirety.

FIELD

The present embodiments generally relate to a cushion therapy device for providing therapeutic relief to a user's back, neck, or combinations thereof.

BACKGROUND

Spinal injuries can be the cause of significant pain to people. Not only are back and spinal injuries relatively easily incurred, but injuries to surrounding musculature can be the cause of significant discomfort or be debilitating to the injured. Injury here refers to damage to the spinal cord and surrounding musculature, inclusive of strains, sprains, and the like.

Typical treatment of back and spinal injuries includes cessation of physical activity and rest.

A significant proportion of the back pain experienced by the general public occurs in the lower back or spinal area. Back injuries can cause significant loss in productivity.

Back injuries can account for nearly forty percent of all work days missed.

A need exists, therefore, for an adjustable cushion therapy device that provides therapeutic relief to a user's back and/or neck that can be attached to a harness, a chair, or a backpack for transportable use.

The present embodiments meet these needs.

BRIEF DESCRIPTION OF THE DRAWINGS

The detailed description will be better understood in conjunction with the accompanying drawings as follows.

Figure 1:
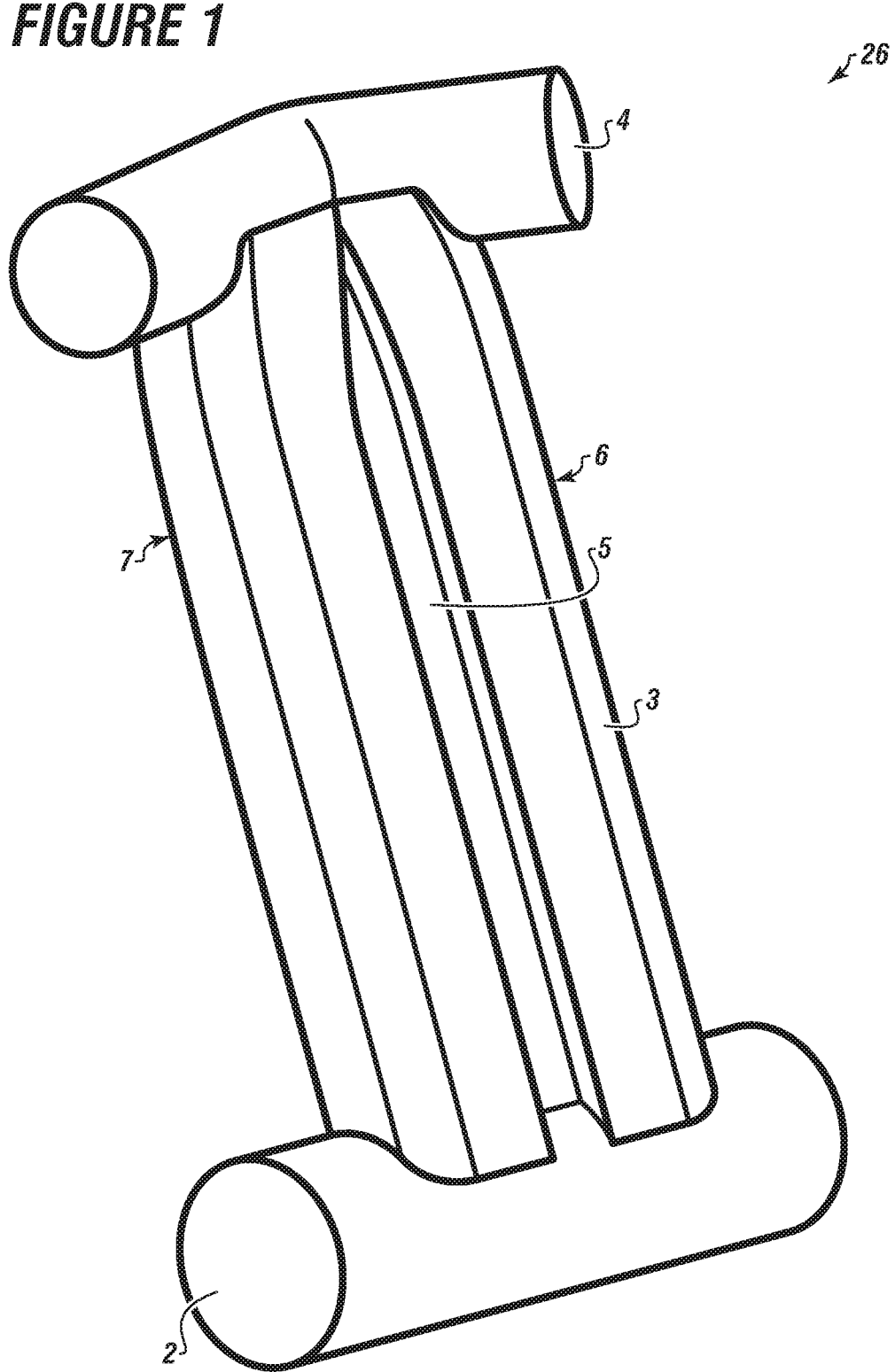
FIG. 1 shows a cushion therapy device according to one or more embodiments.

The present embodiments are detailed below with reference to the listed Figures.

DETAILED DESCRIPTION OF THE EMBODIMENTS

Before explaining the present apparatus in detail, it is to be understood that the apparatus is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is incorporated into the specification as an embodiment of the present disclosure. Thus, the claims are a further description and are an addition to the embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The present embodiments generally relate to a cushion therapy device for providing therapeutic relief to a user's back and/or neck.

The device can provide users as an economical alternative to costly professional physical therapy or surgery by providing therapeutic stress relief and relaxation to users experiencing muscular or skeletal pains, tensions, or other muscular or skeletal ailments. For example, embodiments of the apparatus can be used to decompress stress in a user's back, neck, or combinations thereof, thereby providing the user with greater flexibility, relieving muscular tension, and leading to faster recovery from muscle cramps, aches, and pains. Also, embodiments can be used to remind a user to maintain proper posture.

The cushion therapy device can have a body comprising a channel, an upper member connected to the body, and a lower member connected to the body. The channel can be configured to be placed proximate a user's spine. When used, the bulge of a user's spine can be received within the channel to alleviate any pressure being placed upon the spine.

In embodiments, the cushion therapy device can be one integral piece.

In embodiments, the cushion therapy device comprises foam. Foam refers to a substance created by trapping air pockets within a solid or a liquid. Typically, the present invention refers to foams made from solids. A closed cell or an open cell foam can be utilized based upon the specific application.

Exemplary foams include, but are not limited to: polyurethane, polystyrene, polyethylene, polypropylene, and the like. Persons having ordinary skill in the art can select any applicable foam based upon desired characteristics.

The cushion therapy device can be formed of open cell foam, closed cell foam, polypropylene, polyethylene, polyurethane, polystyrene, an extruded foam polymer, a sponge like material like memory foam, such as viscoelastic polyurethane memory foam, or any other known foam. The material can be water resistant.

The cushion therapy device can have a first rail and a second rail, wherein the first rail and the second rail are on opposite sides of the channel. The rails can contact a user's back while the bulge of the user's spine is received within the channel. The upper member can be positioned proximate the user's neck, and the lower member can be positioned in the lower back region, such as proximate the buttocks. In this manner, pressure is relieved from the spine of the user, and redistributed to other areas of the user's back. This can thereby provide a therapeutic cushioning to the user's back and neck In embodiments, the cushion therapy device can be inflatable. In embodiments, a heating element or a cooling element can be disposed within at least a portion of the cushion therapy device, allowing a user to adjust a temperature of the cushion therapy device.

One or more embodiments relate to a harness with a cushion therapy device, wherein the cushion therapy device can be attached to the harness. The harness can include an attachment means, allowing a user to position the cushion therapy device such that it is disposed proximate the user's back and/or neck. The attachment means can be any known to persons having ordinary skill in the art, such as straps, ties, rubber bands, and the like.

For example, the harness can include a pouch and at least one adjustable webbing strap connected thereto The at least one adjustable webbing strap can include a first adjustable lower webbing strap connected to the pouch and a second adjustable lower webbing strap connected to the pouch. The first adjustable lower webbing strap can be engageable with the second adjustable lower webbing strap. For example, the first adjustable lower webbing strap can connect to the second adjustable lower webbing strap with a strap fastener. The second adjustable lower webbing strap can have a strap fastener, or a first adjustable fastener, that can be configured to engage the first adjustable lower webbing strap.

The at least one adjustable webbing strap can include a first adjustable upper webbing strap connected to the first adjustable lower webbing strap, and a second adjustable upper webbing strap connected to the second adjustable lower webbing strap. The first adjustable upper webbing strap can be engageable with the second adjustable upper webbing strap. The first adjustable lower webbing strap can connect to the first adjustable upper webbing strap with a strap fastener, the second adjustable lower webbing strap can connect to the second adjustable upper webbing strap with a strap fastener, and the first adjustable upper webbing strap can connect to the second adjustable upper webbing strap with a strap fastener. The second adjustable upper webbing strap can have a strap fastener, or a second adjustable fastener, that can be configured to engage the first adjustable upper webbing strap.

The at least one adjustable webbing strap can include a first adjustable shoulder webbing strap connected to the pouch and to the first adjustable upper webbing strap, and a second adjustable shoulder webbing strap connected to the pouch and to the second adjustable upper webbing strap. A first shoulder pad can be connected to the first adjustable shoulder webbing strap, and a second shoulder pad can be connected to the second adjustable shoulder webbing strap.

Each strap fastener can be an adjustable buckle, an adjustable parachute buckle, or another adjustable fastener, such that the user can tighten or loosen the webbing straps to fit the user. Each webbing strap can be made of nylon webbing, a seatbelt material, or another strap material.

A user can wear the harness with the cushion therapy device, thereby providing the user with a mobile cushion. A user wearing the harness with the cushion therapy device can sit or stand against a surface, such as the back of a chair, a floor, or a bed to receive a therapeutic cushioning experience.

In one or more embodiments, the cushion therapy device can be disposed within a fabric portion. The fabric portion can be sewed about a surface of the cushion therapy device. The fabric portion can be sewed directly over the surface of the cushion therapy device and can be flush with the surface of the cushion therapy device, thereby allowing the back and neck cushion therapy device to fit between shoulder straps of a backpack. The fabric portion can be attached to a backpack or a frame of a backpack.

The fabric portion can include at least one strap connected thereto. The at least one strap, or at least one webbing strap, can be configured to be fastened to the backpack or the backpack frame. For example, the at least one strap can be fastened to the backpack, such that when a user wears the backpack, the cushion therapy device within the fabric portion can be disposed between the backpack and the user's back, neck, or combinations thereof, providing a therapeutic cushioning of the weight of the backpack on the user's back and/or neck. The at least one strap can be a webbing strap as described herein. During use, the lower member can absorb the weight of the backpack, and can evenly distribute that weight, thereby simultaneously protecting a user's lower back, upper back, neck, kidneys, and body parts associated with the back and neck region from the pressures exerted by the backpack.

In one or more embodiments, a first cushion therapy device can be located in a first pouch and a second cushion therapy device can be located in a second pouch, the pouches can be attached to each other, providing a reversible therapy device having two cushion therapy devices.

The reversible therapy device having two cushion therapy devices can include a first pouch with at least one side strap. A first cushion therapy device can be at least partially disposed inside the first pouch. The reversible back and neck cushion therapy device can include a second pouch with at least one side strap. A second cushion therapy device can be at least partially disposed inside the second pouch. The second cushion therapy device can have a lower firmness than the first cushion therapy device, thereby providing a reversible therapy device having a soft cushion therapy device and a firm cushion therapy device. During use, if a user wants a firm cushion, the user can dispose the therapy device such that the firm cushion therapy device is disposed directly behind the user's back, neck, or combinations thereof. If the user then wants to change to a soft cushion, the user can dispose the reversible therapy device such that the soft cushion therapy device is disposed directly behind the user's back, neck, or combinations thereof.

The reversible therapy device can include at least one connecting strap connecting between the first pouch and the second pouch, allowing the user to hang the first pouch and the second pouch over a chair, a bed, or a substantially rigid surface. For example, the user can dispose the therapy device over the chair such that either the first pouch or the second pouch is disposed between the user and the chair. A user can interchange different cushion therapy devices within each pouch. For example, a user can have a soft cushion therapy device that the user can use with a harness and pouch. When the user wants a firmer cushion therapy device, the user can remove the soft cushion therapy device and insert the firm cushion therapy device into the pouch.

The at least one side strap of the first pouch can be engageable with the at least one side strap of the second pouch, allowing the user to strap the reversible therapy device to the chair, the bed, or another substantially rigid surface. For example, after the user disposes the reversible therapy device over the back of the chair, the user can attach the at least one side strap of the first pouch and the at least one side strap of the second pouch together using a fastener, such as a hook and loop fastener.

The reversible therapy device can be disposed over a flat rigid surface, such as a floor, allowing the user to receive back and neck stimulation from either the first cushion therapy device or the second cushion therapy device.

In one or more embodiments, each strap of the cushion therapy device can be an elastic strap. The first pouch can include a first side strap and a second side strap. The second pouch can also include a first side strap and a second side strap. The first side strap of the first pouch can be fastened to the first side strap of the second pouch with a fastener, such as a hook and loop fastener. The second side strap of the first pouch can be fastened to the second side strap of the second pouch, such as with a hook and loop fastener.

The cushion therapy device can be attached with a shirt, a backpack, a harness, or the like to allow the user to move and walk about while wearing the cushion therapy device.

The pressure applied by the user's back and/or neck can be applied for any amount of time chosen by the user.

The pressure applied by the user's back can be a variable user-specified pressure. The user can vary the pressure using a weight of at least a portion of the user's body that is in engagement with the cushion therapy device. A user can vary the pressure by applying more pressure or less pressure to the cushion therapy device using the user's back. A user can apply the pressure in a series of pressure cycles to provide a decompressive therapeutic pressure to the user's back and/or neck.

The engagement between the upper member and the body, as well as between the body and the lower member, can be at a variable angle. The variable angle can allow a user to adjust the angle of the engagement to accommodate a position of the user's neck and/or back. For example, during use, if a user leans or bends the user's neck, the variable angle can allow the upper member to bend along with the user's neck, providing support and therapy to the user's neck even when the user's neck is bent. A flexible centralizer can allow the upper and lower members to bend along the variable angle with respect to the body.

Embodiments can include a pressure sensor disposed within or on the cushion therapy device. The pressure sensor can be in electrical communication with an alarm which can also be disposed within or on the cushion therapy device. A preset pressure limit can be a maximum pressure that a user determines should be applied to the cushion therapy device by the user's back and/or neck. The pressure sensor can measure the pressure applied by a user's back and/or neck, and when the pressure applied by the user's back and/or neck exceeds the preset pressure limit, the pressure sensor can send an electronic signal to the alarm to provide an alert to the user. The alert can be an audio signal, such as a sound from a speaker, a visual signal, such as a blinking light, a notification to an electronic device, such as a text message and the like.

Embodiments can include a time sensor which can be actuated to begin measuring time when a user applies pressure to the cushion therapy device. When the user ceases to apply pressure to the cushion therapy device, the time sensor can stop measuring time. A preset time limit can be a maximum time that a user determines pressure should be applied to the cushion therapy device by the user's back and/or neck. The time sensor can measure the usage time in which pressure is applied by a user's back and/or neck. When the usage time exceeds the preset time limit, the time sensor can send an electronic signal to the alarm to provide an alert to the user. The time sensor can be in electrical communication with the alarm, the pressure sensor, or both.

The alarm can provide the alert to the user when the pressure applied by the user's back is greater than a preset pressure limit, when a usage time is greater than a preset time limit, or combinations thereof.

In embodiments, the pressure sensor, the time sensor, and the alarm can be in electrical communication with a processor which can be in electrical communication with a data storage. The preset pressure limit and the preset time limit can be stored on the data storage and can be reprogrammed or adjusted to accommodate various users.

The data storage can have computer instructions stored thereon. The computer instructions can include: computer instructions to compare a measured pressure applied by a user's back and/or neck to the preset pressure limit, computer instructions to compare a measured time to the preset time limit, computer instructions to provide an alarm, and the like.

In embodiments, the cushion therapy device can have a vibration member disposed on it that can produce vibrations for relaxing the user. A power source can be in electrical communication with the vibration member, time sensor, pressure sensor, alarm, processor, data storage, or combinations thereof.

In embodiments, the back and neck cushion therapy device can be customizable. The upper member, body, and lower member can each be shearable, allowing a user to cut the cushion therapy device to a custom size. Users of various ages can have various sizes, shapes, and heights. The customizable cushion therapy device can allow a user to customize a size of the cushion therapy device such that it fits the user's body, thereby allowing a wide variety of users to use the cushion therapy device.

The shearable cushion therapy device can have a plurality of dimensional indicators disposed thereon. The dimensional indicators can provide the user with indications of where to shear or cut the cushion therapy device such that the cushion therapy device is custom sized to fit the particular user. For example, the body can be sheared or cut to fit a length of a particular user's spine.

In embodiments, the upper member, body, and lower member can each have an indentation load deflection ranging from about ten (10) pounds to about eighty (80) pounds, however the upper member, body and lower member can have other indentation load deflections. A twenty five (25) percent indentation load deflection measurement of a upper member, body or lower member can be measured by indenting or compressing the upper member, body or lower member by twenty five (25) percent of its original dimensional magnitude. The amount of force, in pounds, required to indent the upper member, body or lower member by twenty five (25) percent of its original dimensional magnitude is equal to the twenty five (25) percent indentation load deflection. A greater force required to compress the upper member, body or lower member, corresponds to a firmer upper member, body or lower member.

The upper member, body, and lower member can each have a different indentation load deflection or the same indentation load deflection. For example, a user might require a softer body and lower member for placement behind the user's back, and a firmer upper member for placement behind the user's neck. For such uses, the cushion therapy device can have an upper member with a higher indentation load deflection, such as forty (40) pounds, and a body and lower member with a lower indentation load deflection, such as eighteen (18) pounds. Alternatively, the user can have a body and lower member with a higher indentation load deflection, such as forty (40) pounds, and an upper member with a lower indentation load deflection, such as eighteen (18) pounds.

Embodiments of the cushion therapy device can have a density of one and one half (1.5) pounds per cubic foot. However, persons having ordinary skill in the art can adjust densities to suit a specific application.

The cushion therapy device can be customizable, wherein various sizes of upper members with various indentation load deflections can be interchangeable, and can be used with various sizes of interchangeable bodies and lower members with various indentation load deflections.

The body can have a length that can vary from about twelve (12) inches to about thirty (30) inches; however, the body can be other lengths. The upper member can have a length that can vary from about five (5) inches to about seven (7) inches; however, the upper member can be other lengths. The upper member and body can each have a diameter that can vary from about two (2) inches to about five (5) inches.

Turning now to the Figures, FIG. 1 depicts a cushion therapy device according to one or more embodiments.

The cushion therapy device 26 can have a one-piece construction. The cushion therapy device 26 can be made from foam, composite, or the like. The cushion therapy device 26 can include a lower member 2, a body 3, and an upper member 4.

The lower member 2 can have a cross sectional shape, which can be oval. The lower member 2 can have a curvature configured to contour to a person's lower back.

The body 3 can have a cross sectional shape, which can be rectangular. The body 3 can have a channel 5 formed therein. The channel 5 can be configured such that it provides a void that prevents compression pressure from being applied directly to a person's spinal cord when in use. A first rail 6 can sit on the left side of a person's back, and a second rail 7 can sit on a right side of a person's back.

The upper member 4 can have a circular cross section. The upper member 4 can have a contour configured to fit at least partially about a person's neck when the device is worn.

The cushion therapy device 26 can have any desired dimensions. The cushion therapy device 26 can be made from any material. In one or more embodiments, the material can be water resistant.

Figure 2:
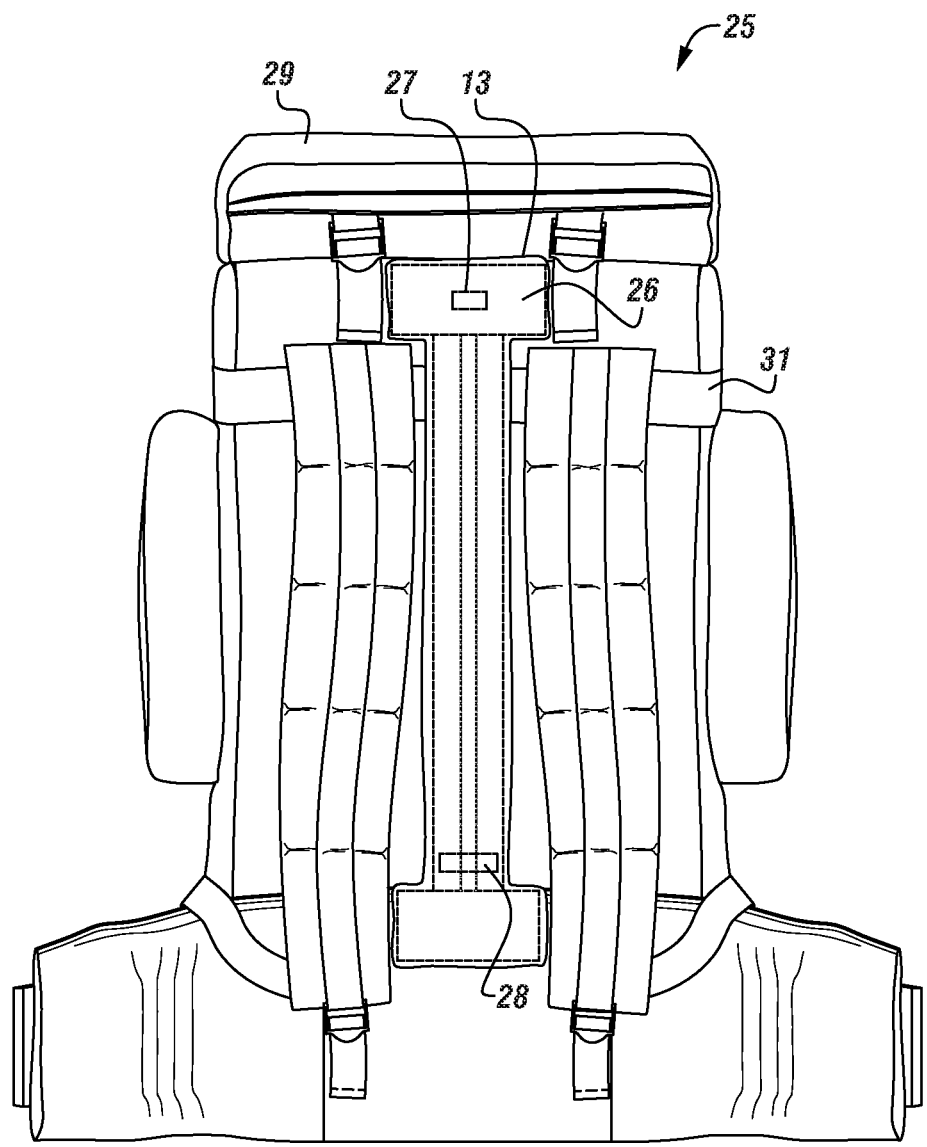
FIG. 2 depicts a backpack with a back and neck cushion therapy device according to one or more embodiments.

FIG. 2 depicts a backpack with a back and neck cushion therapy device according to one or more embodiments.

In this embodiment, the back and neck cushion therapy device 25 can have a fabric portion 13 having a cushion therapy device 26 disposed therein. The fabric portion 13 can be connected to a backpack 29 with a webbing strap 31. In one or more embodiments, the fabric portion 13 can connect to a frame of the backpack with the webbing strap 31. The fabric portion 13 can conform to a surface of the cushion therapy device 26, such that the fabric portion is form fittingly engaged about the surface of the cushion therapy device.

The cushion therapy device 26 can have an additional attachment 27 located anywhere on the body, upper member, or lower member. Exemplary attachments include, but are not limited to: a heating element, a cooling element, or a vibration element. All of these devices can provide additional therapeutic relief to a user. Various therapeutic devices can be chosen by persons having ordinary skill in the art.

The cushion therapy device 26 can have a pressure sensor 28 to detect the amount of pressure applied to, or applied by a user located anywhere on the body, upper member, or lower member.

Figure 3:
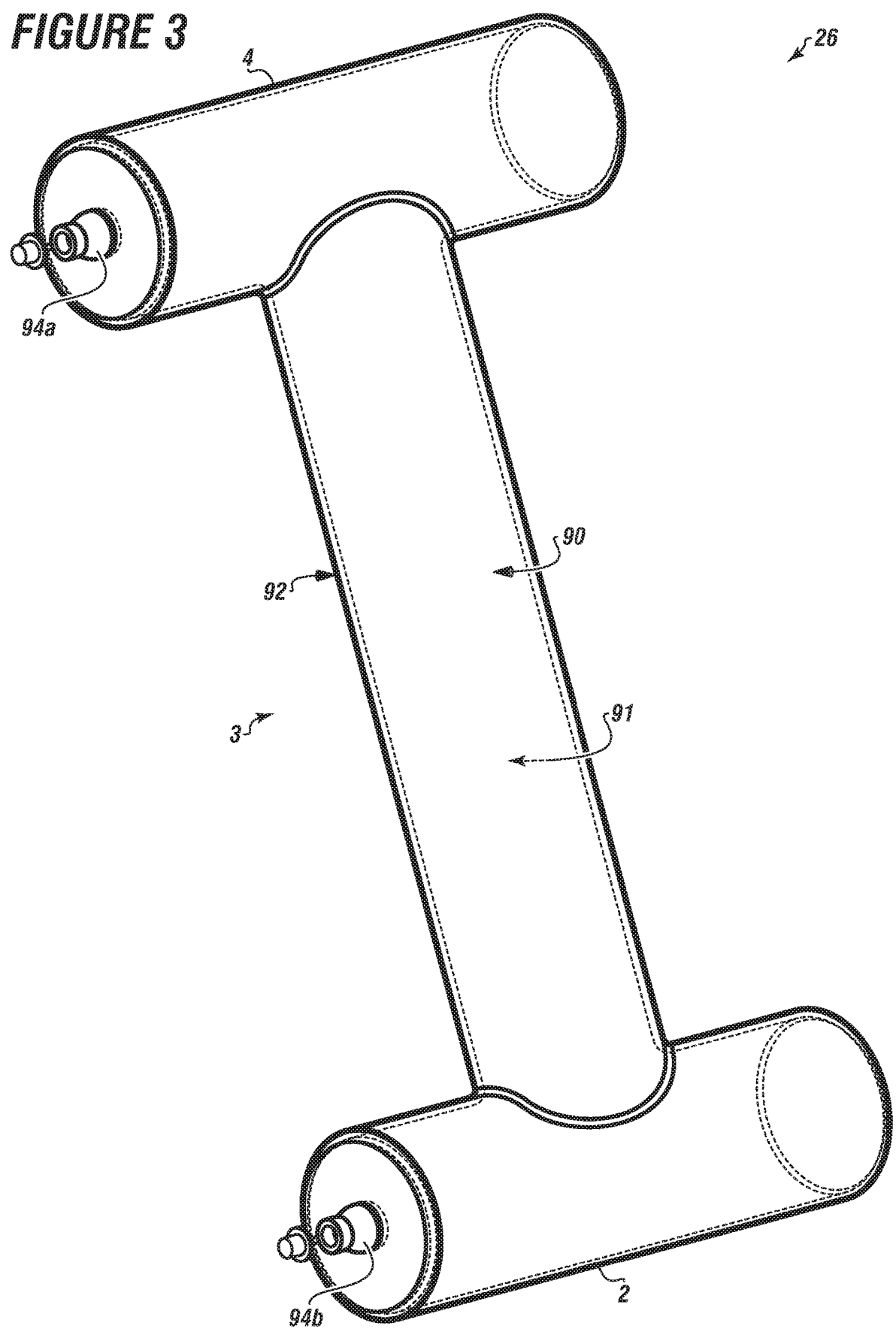
FIG. 3 depicts a cushion therapy device according to one or more embodiments.

FIG. 3 depicts another embodiment of the cushion therapy device.

The cushion therapy device 26 can have an upper member 4, a body 3, and a lower member 2. The upper member 4, the body 3, and the lower member 2 can be made from a material that can expand when an internal pressure is applied to it.

In one or more embodiments, the upper member 4, the body 3, and the lower member 2 can be made from a material that is not air permeable, and the cushion therapy device 26 can be a one-piece construction. A space 91 can be formed between a front side 90 and a back side 92 of the cushion therapy device 26. The space can be configured to receive air and store air. As air is provided to the space, pressure can expand the cushion therapy device 26. The cushion therapy device 26 can be expanded until it is at suitable stiffness for use.

One or more inlets 94a and 94b can be in communication with the space, and the one or more inlets 94a and 94b can be used to provide air to the space 91.

While the present invention has been described with emphasis on the embodiments, it should be understood that within the scope of the appended claims, the invention might be practiced other than as specifically described herein.

What is claimed is:

1. A cushion therapy device comprising:
   a a body comprising a channel, wherein the channel is configured to be placed proximate a user's spine, and further wherein the user's spine is received within the channel along the length of the channel to alleviate any pressure being placed upon the spine;
   b an upper member connected to the body substantially orthogonally to the channel; and c a lower member connected to the body substantially orthogonally to the channel a first rail and a second rail, wherein the first rail and the second rail are on opposite sides of the channel.

2. The cushion therapy device of claim 1, wherein the cushion therapy device comprises foam.

3. The cushion therapy device of claim 1, wherein the cushion therapy device is one piece.

4. The cushion therapy device of claim 1, further comprising a heating element.

5. The cushion therapy device of claim 1, further comprising a cooling element.

6. The cushion therapy device of claim 1, further comprising a pressure sensor.

7. The cushion therapy device of claim 1, further comprising a vibration member.

8. A cushion therapy device comprising:

a a cushion therapy body comprising a channel, wherein a user's spine is received within the channel along the length of the channel to alleviate any pressure being placed upon the spine; a first rail and a second rail, wherein the first rail and the second rail are on opposite sides of the channel;

b a lower member transversely connected with the cushion therapy body; and c an upper member transversely connected with the cushion therapy body opposite the lower member, wherein the cushion therapy body, the lower member, and the upper member are inflatable.

\* \* \* \* \*